United States Patent [19]

Hirschberg et al.

[11] Patent Number: 5,397,341
[45] Date of Patent: Mar. 14, 1995

[54] DEFIBRILLATION ELECTRODE

[75] Inventors: Jakub Hirschberg, Taeby; Heinz Neubauer, Jaerfaella; Nina Gilljam, Bro; Staffan Bowald, Almunge, all of Sweden

[73] Assignee: Siemens Elema AB, Solna, Sweden

[21] Appl. No.: 25,666

[22] Filed: Mar. 3, 1993

[30] Foreign Application Priority Data

Mar. 16, 1992 [SE] Sweden .................. 92008036

[51] Int. Cl.⁶ ................................ A61N 1/05
[52] U.S. Cl. ..................... 607/122; 128/642
[58] Field of Search .............. 128/642; 607/115, 116, 607/119, 122, 123, 126, 128, 130

[56] References Cited

U.S. PATENT DOCUMENTS

| 4,030,509 | 6/1977 | Heilman et al. | |
| 4,522,212 | 6/1985 | Gelinas et al. | 128/642 |
| 4,660,571 | 4/1987 | Hess et al. | |
| 4,699,147 | 10/1987 | Chilson et al. | 128/642 |
| 4,860,769 | 8/1989 | Fogarty et al. | |
| 4,940,064 | 7/1990 | Desai. | |
| 5,010,894 | 4/1991 | Edhag. | |
| 5,127,421 | 7/1992 | Bush et al. | 607/122 |
| 5,156,151 | 10/1992 | Imran | 607/122 X |
| 5,228,442 | 7/1993 | Imran | 607/122 X |

FOREIGN PATENT DOCUMENTS 0009732 9/1979 European Pat. Off. .
0426089 10/1990 European Pat. Off. .
0479435 9/1991 European Pat. Off. .

Primary Examiner—Lee S. Cohen
Assistant Examiner—Jeffrey R. Jastrzab
Attorney, Agent, or Firm—Hill, Steadman & Simpson

[57] ABSTRACT

A defibrillation electrode has a flexible electrode cable containing at least one elongated, electrically insulated conductors and having an electrode configuration attached at a distal end of the electrode cable. This electrode device configuration a number of elongated, flexible conductors, pre-shaped into an outward bulging configuration, having first ends anchored adjacent to each other at the distal end of the electrode cable, and second ends anchored adjacent to each other at a common connection point. To attain a defibrillation electrode which can be used for intracardial, epicardial and myocardial stimulation of the heart and which can be rapidly introduced into the patient, and applied to the myocardium or pericardium, with no need for major surgery, the conductors are spatially pre-shaped such that the anchored ends at the common connection point are twisted in relation to the anchored ends at the electrode cable's distal end. A device is provided for varying the relative distance between the conductors' anchored ends at the common connection point and the conductors' anchored ends at the distal end of the electrode cable.

11 Claims, 2 Drawing Sheets

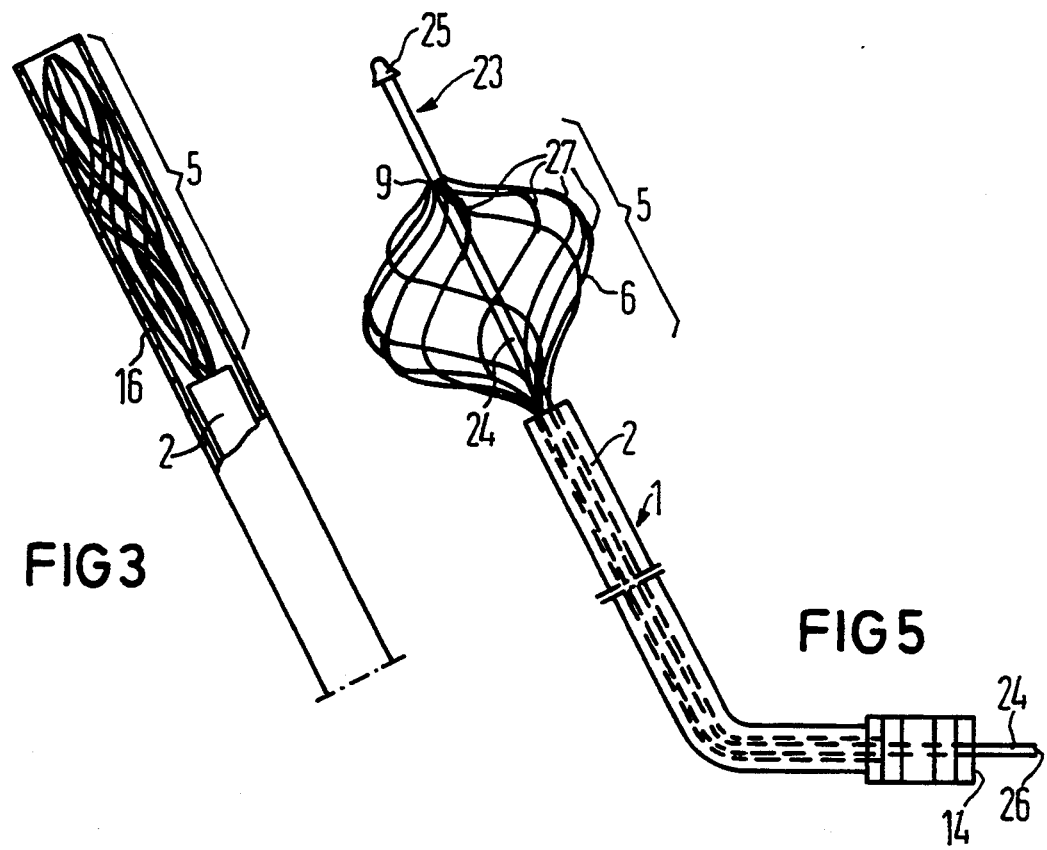
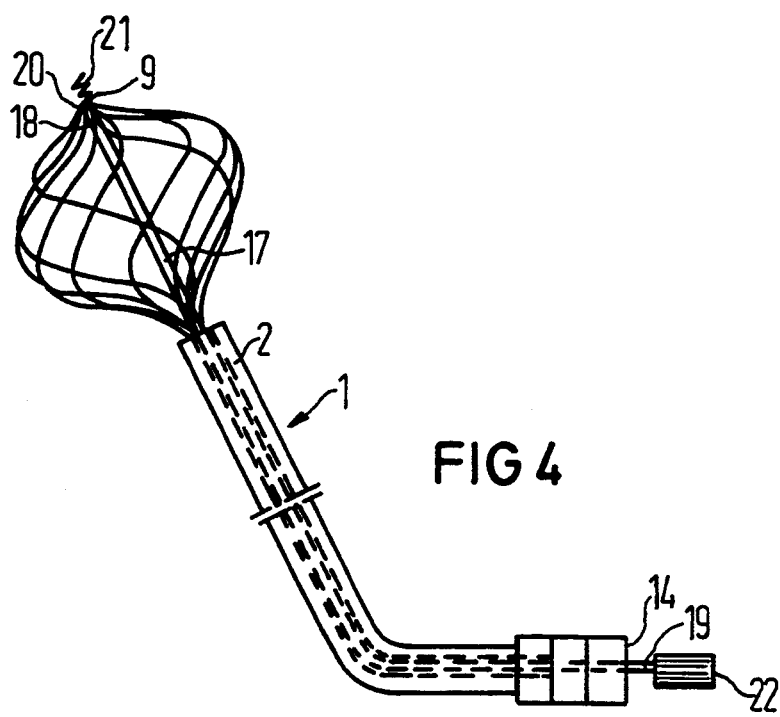

DEFIBRILLATION ELECTRODE

BACKGROUND OF THE INVENTION

1. Field of the Invention

The present invention relates to a defibrillation electrode for in vivo use of the type having a flexible electrode cable containing at least one elongated, electrically insulated conductor, and an electrode device, attached to the distal end (i.e., opposite the end of the cable connectable to the implantable housing) of the electrode cable, containing a plurality of elongate, flexible conductors, pre-shaped into an outward bulging configuration, the conductors having first ends anchored adjacent to each other at the distal end of the electrode cable, and second ends anchored adjacent to each other at a common connection point.

2. Description of the Prior Art

One such defibrillation electrode known in the art is described in U.S. Pat. No. 5,010,894. This defibrillation electrode, which can also be combined with a pacemaker electrode, is designed solely for intracardial stimulation of the heart. Before the introduction of the electrode into a vein, the pre-shaped conductors of the electrode device are extended with the aid of a stylet, bringing them close together and enabling introduction into the heart without damage to venous walls.

U.S. Pat. No. 4,030,509 discloses a patch-type defibrillation electrode. Such a patch electrode is applied directly to the myocardium or pericardium and is not designed nor intended for introduction into the heart.

SUMMARY OF THE INVENTION

An object of the present invention is to provide a defibrillation electrode of the type described above which can be employed both for intracardial and epicardial stimulation of the heart and can be introduced into the patient and applied to the epicardium or pericardium quickly and without extensive surgery.

The above object is achieved in accordance with the principles of the present invention in a defibrillation electrode for in vivo use having electrode means for electrically interacting with tissue to be stimulated, the electrode means being formed by spatially pre-curved conductors having ends anchored at a common connection point which are twisted, by virtue of the pre-curving, in relation to opposite ends of the conductors which are anchored at the electrode cable's distal end, and the electrode further includes means for varying the relative distance between the conductors' anchored ends at the common connection point and the conductors' anchored ends at the distal end of the electrode cable. As a result of this structure, the conductors can be extended, thereby reducing their common external diameter, so the electrode means can be introduced into the heart via a vein or applied to the pericardium or outer wall of the heart. With the distance varying means, the distance between the anchored ends of the conductors can be reduced so the conductors assume a virtually two-dimensional electrode configuration which, as a result of the above described twisting of the conductors' anchored ends at the common connection point in relation to the anchored ends at the electrode cable's distal end, is shaped like overlapping flower petals. In this manner, a patch electrode of varying size, depending on the length of the conductors, is obtained. The density of the patch electrode is governed by the number of conductors in the electrode means. Since the external diameter of the defibrillation electrode is small during introduction into the patient, the surgical procedure required therefor is relatively slight. The defibrillation electrode can also be applied and held to advantage in the superior or inferior vena cava by tensioning the conductors against the venous walls.

In an embodiment of the invention, the distance varying means is formed by a line which can be pulled back and forth in the electrode cable and having a distal end attached to the common connection point of the conductors and having a proximal end extending beyond the proximal end of the electrode cable. Such a line can be very thin and flexible, so that this line would not affect the flexibility of the electrode conductor.

Alternately, the distance varying means may be formed by a stylet which slides in the electrode cable, having a distal end attached to the common connection point and a proximal end extending beyond the proximal end of the electrode cable. The conductors can be extended through the stylet, in contrast to the line, in such a way that the external diameter of the electrode means is reduced, enabling it and the electrode cable to be introduced into and through a vein.

In a preferred embodiment of the invention, the conductors' anchored ends at the common connection point are twisted at an angle of 120° to 240°, preferably 180°, in relation to the anchored ends at the electrode cable's distal end. A twist angle must be selected so that the conductors, when the distance between the anchored ends is reduced, are roughly perpendicular to the longitudinal axis of the electrode cable and partially overlap each other.

In another embodiment of the invention, the common connection point, consists of an interconnection element. This element could be a plate on which, e.g., an attachment device can be mounted. When the defibrillation electrode is used in the form of a patch electrode, a helical tip, which is screwed into myocardium with the aid of a stylet, could be mounted on the interconnection element.

In another embodiment of the invention, the conductors of the electrode means could be partially insulated. Such insulation could be advantageous when the defibrillation electrode is used as an intracardial electrode and when the conductors are extended between the heart walls in the ventricle. The parts of the conductors touching the heart walls could be insulated to advantage, thereby preventing burn damage to the tissue.

In a further embodiment of the invention the defibrillation electrode can be combined with a pacemaker electrode whose stimulation surface is applied near the conductors' connection point. A combined form of this kind is suitable for an intracardial defibrillation electrode.

In a simple embodiment of the invention the pacemaker electrode's cable serves as a means for varying the relative distance between the conductors' anchored ends at the common connection point and the conductors' anchored ends at the electrode cable's distal end.

In another embodiment of the invention, the electrode means can slide in a catheter having a lumen which is only slightly larger than the external diameter of the electrode cable. As a result, the defibrillation electrode can be introduced into the patient with no damage inflicted on venous walls or other tissue by protruding conductors.

DESCRIPTION OF THE DRAWINGS

FIG. 3 is a side view of the electrode means according to FIGS. 1 and 2 used with an introducer.

FIGS. 4 and 5 respectively shown further embodiments of the defibrillation electrode according to FIGS. 1 to 3.

DESCRIPTION OF THE PREFERRED EMBODIMENTS

Figure 1:
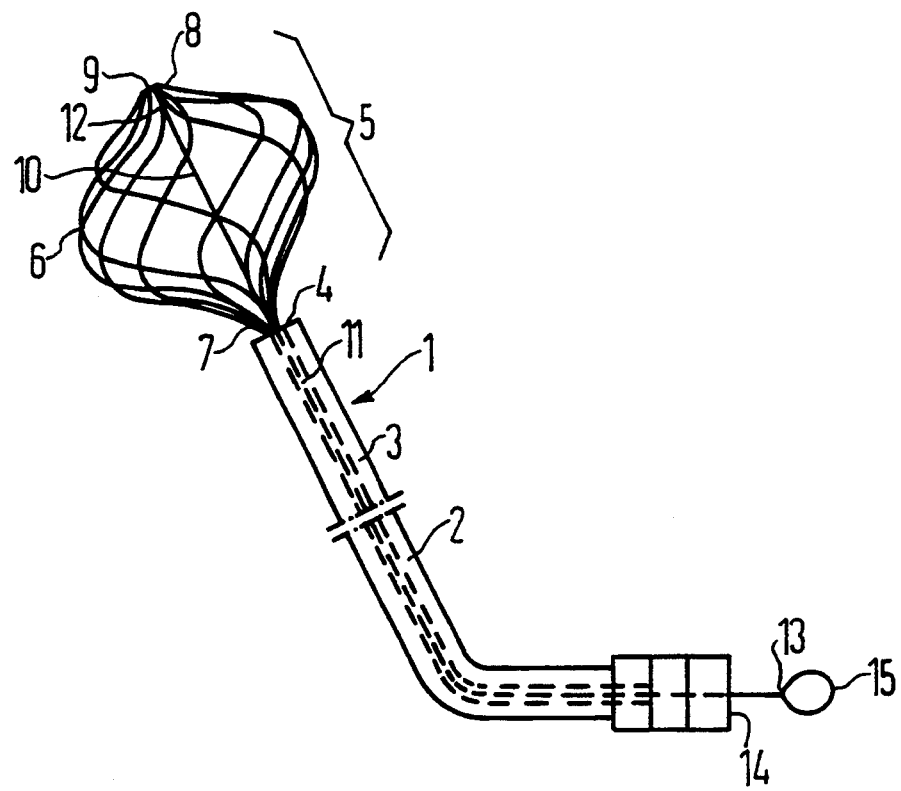
FIG. 1 is a side view of a defibrillation electrode with an electrode means constructed in accordance with the principles of the present invention.

A defibrillation electrode 1 for in vivo use is shown in FIG. 1, having a flexible electrode cable 2, containing elongated, electrically insulated conductors 3 which are anchored to an electrode means 5 attached at the distal end 4 of the electrode cable 2. The electrode means 5 consists of a plurality of elongated, flexible conductors 6, pre-shaped into an outward bulging configuration. The conductors 6 have respective first ends 7 anchored adjacent to each other at the electrode cable's 2 distal end 4, and opposite, second ends 8 anchored adjacent to each other at a common connection point 9. The conductors 6 are also spatially curved in such a way that their anchored ends 8 at the common connection point 9 are twisted in relation to their anchored ends 7 at the distal end 4 of the electrode cable 2. The twist angle is in the range from approximately 120° to approximately 240°, preferably 180°. The defibrillation electrode 1 is equipped with a line 10 which runs in and along the electrode cable 2, e.g., in a tunnel 11 formed by spirally coiled conductors 3. The distal end 12 of the line 10 is attached to the connection point 9, and its proximal end 13 extends beyond the electrode cable's 2 proximal end 14. The proximal end 13 of the line 10 can be equipped to advantage with a device, such as a loop 15, providing a better hold for the operator. The relative distance between the anchored ends 8 of the conductors 6 at the common connection point 9 and anchored ends 7 of the conductors 6 at the distal end 4 of the electrode cable 2 varies when the operator pulls on the line 10.

Figure 2:
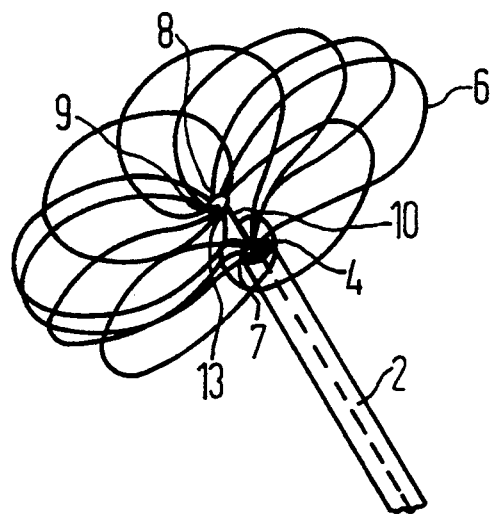
FIG. 2 is a perspective view of another embodiment of the electrode means according to FIG. 1.

FIG. 2 shows that when the distance between the opposite anchored ends 7 and 8 of the conductors 6 is greatly reduced, the conductors 6 assume a virtually two-dimensional electrode configuration shaped like overlapping flower petals. The defibrillation electrode described in FIGS. 1 and 2 can be used to advantage in the form as a patch electrode applied to the outer wall of the myocardium or to the pericardium. This defibrillation electrode 1 can be used even for intracardial defibrillation, in which the shape of the electrode device 5 is controlled with the aid of the line 10.

When the defibrillation electrode 1 is introduced into a patient's heart through a vein, an introducer or catheter 16 can be used in which the electrode device 5 and at least parts of the electrode cable 2 are fitted, as illustrated in FIG. 3. Here, the lumen of the catheter 16 is only slightly larger than the external diameter of the electrode cable 2 so the electrode device 5 can be introduced into the ventricle without the conductors 6 inflicting damage on the heart or walls of the heart. When the defibrillation electrode 1 is in position in the ventricle, the electrode device 5 is released by reversing the catheter 16, using a known device (not shown), or by advancing the electrode device 5 inside the catheter 16, whereupon the electrode device 5 assumes the pre-shaped configuration as illustrated in FIG. 1. A defibrillation electrode of this kind can also be applied in the superior or inferior vena cava.

In FIG. 4, the defibrillation electrode 1 is fitted with a stylet 17 which replaces the line 10. The stylet 17, like the line 10, can be slid within the electrode cable 2. The stylet 17 has a rotatable distal end 18 attached to the connection point 9, and a proximal end 19 extending beyond the electrode cable's 2 proximal end 14. In this embodiment, the connection point 9 consists of an interconnection element 20 in the form of a plate which serves as a support for a rotating helical tip 21 which is attached to the plate 20. The helical tip 21 is attached to the stylet 17. Rotating a knob 22 attached to the proximal end 19 of the stylet 17, in one direction turns the tip 21 to the corresponding degree in the same direction. This defibrillation electrode is especially suitable for use in the form of a patch electrode, the tip 21 serving as an attachment device.

The above described stylet 17 can also be used to advantage with the defibrillator electrode 1 illustrated in FIGS. 1 and 2. In contrast to the line 10, the stylet 17 is able to extend the electrode device 5 in such a way that the conductors 6 are together along their length inside this stylet 17. In this way, the defibrillation electrode 1 can be introduced into the patient without the aid of a catheter 16.

The defibrillation electrode 1 illustrated in FIG. 5 is combined with a pacemaker electrode 23, having an electrode cable 24 which can slide inside the cable 2 of the defibrillation electrode 1. The cable 24 of the pacemaker electrode 23 is attached to the connection point 9 of the electrode means 5 terminates with an electrode head 25 for transmission of stimulation pulses to the heart which slides out beyond the connection point 9 to bear against the heart wall. In this embodiment, the cable 24 of the pacemaker electrode 23, whose proximal end 26 extends beyond the proximal end 14 of the cable 2, serves as the means for varying the relative distance between the anchored ends 7 and 8 of the conductors 6. The above described defibrillation electrode is especially designed for intracardial defibrillation of the heart with concomitant cardiac stimulation with a pacemaker. The parts 27 of the conductors 6 bearing against the heart walls can be insulated to advantage to prevent burn damage to tissue.

The catheter 16 illustrated in FIG. 3 can also be used in conjunction with the defibrillation electrodes illustrated in FIGS. 4 and 5.

The length of the described electrode means, i.e., the length of the conductors 6, can be varied, especially when the defibrillation electrode is used as a patch electrode, so as to obtain a stimulation surface of varying size. The number of conductors can also be varied so as to achieve a patch electrode of varying density. The conductors 6, which can consist of single, spun or helical wires, can be insulated in such a way that different electrode surface shapes and sizes and the desired number of stimulation surfaces are obtained when the electrode device is in the extended position.

The defibrillation electrode according to the invention can also be applied subcutaneously, subpleurally or intercostally, to the chest wall, in addition to the sites described above.

Although modifications and changes may be suggested by those skilled in the art, it is the intention of the inventor to embody within the patent warranted hereon all changes and modifications as reasonably and properly come within the scope of his contribution to the art.

We claim as our invention:

1. A defibrillation electrode for in vivo use comprising:
   a cable having at least one elongated insulated conductor terminating at a distal end of said cable;
   electrode means for electrically interacting with tissue in vivo formed by a plurality of elongated flexible conductors having respective first ends anchored at said distal end of said cable and electrically connected to said conductor in said cable, and respective second ends connected at a common connection point separate from said distal end of said cable, said flexible conductors being pre-shaped into an outwardly bulging configuration and each having a spatial curve so that said second ends at said common connection point are twisted relative to said first ends at said distal end of said cable; and
   manipulable means for selectively varying a distance between said common connection point and said distal end of said cable for causing said conductors to form a substantially two-dimensional electrode configuration when said distance is reduced.

2. A defibrillation electrode as claimed in claim 1 wherein said cable has a proximal end, opposite said distal end, and wherein said manipulable means comprises an element disposed for sliding inside said electrode means and terminating in a manipulable means distal end attached to said common connection point, said element having a proximal end extending beyond said proximal end of said cable.

3. A defibrillation electrode as claimed in claim 2 wherein said element comprises a stylet disposed for sliding inside said electrode means and terminating in a stylet distal end attached to said common connection point, said stylet having a proximal end extending beyond said proximal end of said cable.

4. A defibrillation electrode as claimed in claim 1 wherein said second ends of said flexible conductors at said common connecting point are twisted relative to said first ends at said distal end of said cable at an angle in a range between approximately 120° and approximately 240°.

5. A defibrillation electrode as claimed in claim 1 wherein said second ends of said flexible conductors connected at said common connection point are twisted relative to said first ends anchored at said distal end of said cable, at an angle of approximately 180°.

6. A defibrillation electrode as claimed in claim 1 wherein said common connection point comprises an interconnection element.

7. A defibrillation electrode as claimed in claim 1 wherein said flexible conductors are partially insulated.

8. A defibrillation electrode as claimed in claim 1 further comprising a pacing electrode having a stimulation surface disposed in the region of said common connection point.

9. A defibrillation electrode as claimed in claim 8 wherein said pacing electrode has a cable, and wherein said cable of said pacing electrode comprises said manipulable means.

10. A defibrillation electrode as claimed in claim 1 further comprising a catheter disposed at said distal end of said cable, said catheter having a lumen which is slightly larger than an external diameter of said cable, and said electrode means being disposed for sliding inside said catheter.

11. A defibrillation electrode as claimed in claim 1 wherein said flexible conductors are pre-shaped and are anchored at their first and second ends for forming a substantially two-dimensional electrode configuration with said conductors forming overlapping petals when said distance between said common connection point and said distal end of said cable is reduced.

* * * * *